United States Patent [19]
Brown et al.

[11] Patent Number: 5,914,316
[45] Date of Patent: Jun. 22, 1999

[54] METHOD OF INHIBITING INTIMAL HYPERPLASIA

[75] Inventors: David M. Brown; Tze-Chein Wun; Roger K. Khouri, all of St. Louis, Mo.

[73] Assignee: Washington University, St. Louis, Mo.

[21] Appl. No.: 08/719,594

[22] Filed: Sep. 25, 1996

Related U.S. Application Data

[63] Continuation of application No. 08/357,806, Dec. 16, 1994, abandoned.

[51] Int. Cl.$^6$ ..................................................... A61K 38/00
[52] U.S. Cl. .................................................. 514/12; 514/8
[58] Field of Search ........................................... 514/12, 8

[56] References Cited

U.S. PATENT DOCUMENTS

| | | | |
|---|---|---|---|
| 4,966,852 | 10/1990 | Wun et al. | 435/235 |
| 5,106,833 | 4/1992 | Broze et al. | 514/12 |
| 5,212,091 | 5/1993 | Diaz-Collier et al. | 435/69 |
| 5,276,015 | 1/1994 | Khouri et al. | 514/12 |
| 5,385,885 | 1/1995 | Gask et al. | 514/12 |

FOREIGN PATENT DOCUMENTS

WO 93/24143 12/1993 WIPO.
WO 93/25230 12/1993 WIPO.

OTHER PUBLICATIONS

U.S. application No. 08/093,285, Abstract, G.J. Broze, filed Jul. 23, 1987.
Broze and Miletich, *Proc.Natl.Acad.Sci. U.S.A.* 84, 1886–1890 (1987).
Novotny et al, *J.Biol.Chem.* 264, 18832–18837 (1990).
Wun et al, *J.Biol.Chem.* 265, 16096–16101 (1990).
Wun et al, *J.Biol.Chem.* 263, 6001–6004 (1990).
Girard et al, *Thromb.Res.*55, 37–50 (1989).
Girard et al, *Nature* 328, 518–520 (1989).
Rapaport, *Blood* 73, 259–365 (1989).
Broze et al., *Biochemistry* 29, 7539–7546 (1990).
Day et al, *Blood* 76, 1538–1545 (1990).
Pedersen et al, *J.Biol.Chem.* 265, 16786–16793 (1990).
Haskel et al, *Circulation* 84, 821–827 (1991).
Wun et al, *Thromb.Hemostat.* 68, 54–59 (1992), Cold Spring Lab.
Sprecher et al, *Proc.Natl.Acad.Sci. USA* 91, 3353–3357 (1994).
Cooley & Hansen, Microsurgery 6 (46–48,(1985).
Cooley & Gould, Microsurgery 12, pp. 281–287 (1991).
Broze et al., Biochemistry 29, 7539–7546 (1990).

*Primary Examiner*—Cecilia J. Tsang
*Assistant Examiner*—C. Delacroix-Muirhead
*Attorney, Agent, or Firm*—Dennis A. Bennett; Scott J. Meyer

[57] ABSTRACT

A method is disclosed for inhibiting intimal hyperplasia in a warm-blooded mammal which comprises administering topically at the site and time of a vascular injury induced by arterial intervention in said mammal a small but inhibitorily effective amount of tissue factor pathway inhibitor (TFPI) sufficient to inhibit said intimal hyperplasia.

7 Claims, 3 Drawing Sheets

METHOD OF INHIBITING INTIMAL HYPERPLASIA

This is a file-wrapper continuation of application Ser. No. 08/357,806 filed Dec. 16, 1994 now abandoned.

BACKGROUND OF THE INVENTION

This invention relates to a method of inhibiting intimal hyperplasia. More particularly, the invention concerns a method for inhibiting intimal hyperplasia induced by arterial interventions by administering topically at the site and at the time of the vascular injury a blood coagulation inhibitor known as tissue factor pathway inhibitor (TFPI).

As used herein, intimal hyperplasia (also referred to as neointimal hyperplasia) refers to the proliferative response to a vascular injury consisting almost entirely, although not exclusively, of smooth muscle cells (SMCs) which form an intimal lesion on the luminal surface around the inner circumference of a blood vessel (intima) following an arterial intervention such as, e.g., angioplasty or endarterectomy. This tissue ingrowth gradually encroaching into the lumen of the blood vessel is the leading cause of restenosis. Hyperplasia occurs gradually over a period of days to several weeks following the arterial intervention, as distinguished from a thrombus, such as may occur in the circulating blood immediately at the time of intervention.

Note: various literature references on the following background information and on conventional surgical and laboratory procedures well known to the person skilled in the art and other such state-of-the-art techniques as used herein are indicated by numbers in parentheses and appended at the end of the specification, ie., (1) to (62).

It is estimated that well over one million arterial interventions are performed each year in the United States for the treatment of occlusive arterial disease. This includes over

- 300,000 coronary artery bypass surgeries
- 300,000 percutaneous transluminal coronary angioplasties
- 200,000 carotid endarterectomies
- 200,000 peripheral vascular bypass surgeries, and
- 100,000 to 200,000 other invasive procedures which blast burn, or break the occlusive plague (e.g., peripheral arterial angioplasties, laser ablation, intravascular stents, See (1), (2) (3).

The early results of these procedures are generally excellent. However, within six months to five years, over 50% of the treated arteries develop restenosis and require reintervention (4–17). Most develop restenosis within the first year. Consequently, in many clinics, up to 50% of the case load consists of secondary procedures as opposed to first interventions. Restenosis is the reoccurrence of stenosis (reduction of luminal diameter) following manipulation of the arterial wall during surgery.

The restenosis rate varies by procedure and location. Restenosis occurs in 40% to 60% of patients within six months after percutaneous transluminal coronary angioplasty (PTCA) (4–8). The incidence of restenosis after carotid endarterectomy is approximately 30% at five years (9). Saphenous vein aorta-to-coronary grafts have a restenosis rate of 30% at five years and 70% at ten years (10–14). Following femoropopliteal bypass with vein grafts, the restenosis rate is between 30–40% at five years, and when prosthetic bypass grafts are used, between 50–60% (15–17).

Intimal hyperplasia is the principal cause of restenosis following arterial interventions (18–20). Intimal hyperplasia is the result of a complex series of biological processes initiated by arterial injury followed by platelet aggregation and thrombus formation with a final pathway of smooth muscle cell migration and proliferation and extracellular matrix deposition. Platelets adhere and aggregate at the site of injury and release biologically active substances, the most important of which are platelet-derived growth factors (21).

Thrombosis occurs from activation of the coagulation pathways (22). It has been postulated that intimal hyperplasia production is driven by two principal mechanisms platelet activation with the release of platelet-derived growth factors, and activation of the coagulation cascade with thrombus formation, which also results in the release of biologically active substances which can contribute to smooth muscle cell proliferation (23–32). Platelet-derived growth factors and components of the coagulation cascade are known stimulants of smooth muscle-cell growth (33–38).

Antiplatelet agents (e.g. aspirin, arachidonic acid, prostacyclin), antibodies to platelet-derived growth factors, and antithrombotic agents (e.g. heparina low molecular weight heparins) are potent inhibitors of smooth muscle growth (47,49–55). However, clinical trials have shown little effect of these agents on the rate of restenosis (55–62). One can only speculate as to why clinical trials have failed thus far, but two explanations seem plausible.

First, the dose of the agent delivered to the site of injury may have been inadequate. For instance, although thrombocytopenia substantially inhibits intimal hyperplasia in animals, antiplatelet agents have been ineffective in humans it is likely that the dose of antiplatelet agents at the site of injury is inadequate to completely prevent platelet adhesion. Secondly the timing of the drug administration may be inappropriate. Most drugs are given after the injured vessel surface has been exposed to blood and the biological processes which lead to intimal hyperplasia have been initiated.

Tissue factor pathway inhibitor (TFPI) is a naturally occurring glycoprotein inhibitor of the extrinsic pathway of coagulation (39–42). TFPI has been shown to inhibit Factor Xa directly and together with Factor Xa bind and inhibit tissue factor VIIa (39,43).

The name, tissue factor pathway inhibitor (TFPI) has been accepted by the International Society on Thrombosis and Hemostasis, Jun. 30, 1991, Amsterdam. TFPI was previously known as lipoprotein-associated coagulation inhibitor (LACM) TFPI was first purified from a human hepatoma cell, Hep G2 as described by Broze and Miletich, *Proc. Natl. Acad. Sci. USA* 84, 1886–1890 (1987), and subsequently from human plasma as reported by Novotny et al., *J. Biol. Chem.* 264, 18832–18837 (1989); and Chang liver and SK hepatoma cells as disclosed by Wun et al., *J. Biol. Chem.* 265, 16096–16101 (1990). TFPI cDNA have been isolated from placental and endothelial cDNA libraries as described by Wun et al., *J. Biol. Chem.* 263, 6001–6004 (1988); and Girard et al., *Thromb. Res.* 55, 37–50 (1989). The primary amino acid sequence of TFPI, deduced from the cDNA sequence, shows that TFPI contains a highly negatively charged amino-terminus, three tandem Kunitz-type inhibitory domains, and a highly positively charged carboxyl terminus. The first Kunitz domain of TFPI is needed for the inhibition of the factor $VII_a$/tissue factor complex, and the second Kunitz domain of TFPI is responsible for the inhibition of factor $X_a$ according to Girard et al., *Nature* 328, 518–520 (1989), while the function of the third Kunitz domain remains unknown. See also U.S. Pat. No. 5,106,833. TFPI is believed to function in vivo to limit the initiation of coagulation by forming an inert, quaternary factor $X_a$: TFPI:

factor VII$_a$: tissue factor complex. Further background information on TFPI can be had by reference to the recent reviews by Rapaport, *Blood* 73, 359–365 (1989); and Broze et al., *Biochemistry* 29, 7539–7546 (1990).

Recombinant TFPI has been expressed as a glycosylated protein using mammalian cell hosts including mouse C127 cells as disclosed by Day et al., *Blood* 76, 1538–1545 (1990), baby hamster kidney cells as reported by Pedersen et al., *J. Biol. Chem.* 265, 16786–16793 (1990), Chinese hamster ovary cells and human SK hepatoma cells. The C127 TFPI has been used in animal studies and was shown to be effective in the inhibition of tissue factor-induced intravascular coagulation in rabbits according to Day et al., supra, and in the prevention of arterial reocclusion after thrombolysis in dogs as described by Haskel et al., *Circulation* 84, 821–827 (1991).

Recombinant TFPI also has been expressed as a nonglycosylated protein using *E. coli* host cells and obtaining a highly active TFPI by in vitro folding of the protein as described in U.S. Pat. No. 5,212,091, the disclosure of which is incorporated by reference herein. See also Wun et al., *Thromb. Hemostas.* 68, 54–59 (1992).

The cloning of the TFPI CDNA which encodes a 31,950-Dalton protein of 276-amino acid residues with three potential glycosylation sites is further described in Wun at al., U.S. Pat. No. 4,966,852, and allowed application Ser. No. 08/093,285, the disclosures of which are incorporated by reference herein.

Recently, TFPI obtained through recombinant DNA clones expressed in *E. coli* as disclosed in U.S. Pat. No. 5,212,091 has been described as useful for reducing the thrombogenicity of microvascular anastomoses. In the disclosed microvascular surgery, it was desired to keep a very small vessel open for a short time and apply the TFPI topically to prevent thrombus formation. See U.S. Pat. No. 5,276,015, the disclosure of which is incorporated herein by reference.

The use of TFPI for treatment of sepsis or septic shock and sepsis-associated disorders is described in recently published patent applications PCT WO 93/24143 and PCT WO 93/25230.

In a model of vascular thrombosis a single application of TFPI by local irrigation prior to blood reflow prevented platelet adhesion and arterial thrombotic occlusion as determined after 24 hours (44,45). However, that study determined only the inhibition in the formation of a platelet plug within 24 hours as distinguished from end-stage intimal hyperplasia.

Recently, it has been reported that specific inhibition of Factor Xa with recombinant antistatin (rATS) or tick anticoagulant peptide (rTAP) reduces intimal hyperplasia after balloon angioplasty (46,47).

BRIEF DESCRIPTION OF THE INVENTION

In accordance with the present invention a novel method is provided for inhibiting intimal hyperplasia. The method comprises administering to a warm-blooded mammal topically, at the site and time of a vascular injury induced by an arterial intervention, a small but effective amount of tissue factor pathway inhibitor (TFPI) sufficient to inhibit the intimal hyperplasia. By this method of administration, which coats the injured surface with TFPI prior to exposure to circulating platelets and inflammatory cells, a novel preemptive treatment is provided that blocks the initiation of biological events that would otherwise lead to intimal hyperplasia.

The illustrative procedures employed herein were designed.

(a) To show that the administration of TFPI acutely and topically applied to a laboratory rabbit model was able to prevent intimal hyperplasia after arterial interventions of several different types; and (b) To examine TFPI binding and the early sequence of events following a vascular anastomosis.

Many methods of measurement for the quantification of intimal hyperplasia have been reported in the literature. In the laboratory work described herein, the maximal encroachment on the neointimal lesion into the lumen was measured, because this is the portion of the lesion that causes the most disruption in blood flow.

By use of the method of the invention it was found that TFPI specifically and irreversibly binds to the injured vessel wall surface. This appeared to induce the formation of a pacifying scab over the thrombogenic surface, which prevents platelet aggregation and thrombus formation, and inhibits the initiation of the sequence of events that lead to intimal hyperplasia.

The various types of arterial interventions for which the method of the invention is useful include, for example, medical procedures such as:

angioplasty, e.g., balloon angioplasty, laser angioplasty, intravascular stents, which are exemplified herein by an animal model for balloon angioplasty;

endarterectomy, illustrated herein by an animal model for intimectomy, and vascular anastomosis such as bypass graft and arteriovenous fistula.

Although the method of the invention is illustrated herein on laboratory rabbits, it will be appreciated that the method of the invention is useful for other warm-blooded mammals, e.g., humans, in an analogous manner.

As defined herein, TFPI can be either glycosylated or nonglycosylated.

DETAILED DESCRIPTION OF THE INVENTION

While the specification concludes with claims particularly pointing out and distinctly claiming the subject matter regarded as forming the invention, it is believed that the invention will be better understood from the following detailed description of illustrative embodiments of the invention taken in conjunction with the accompanying drawings.

Figure 1:
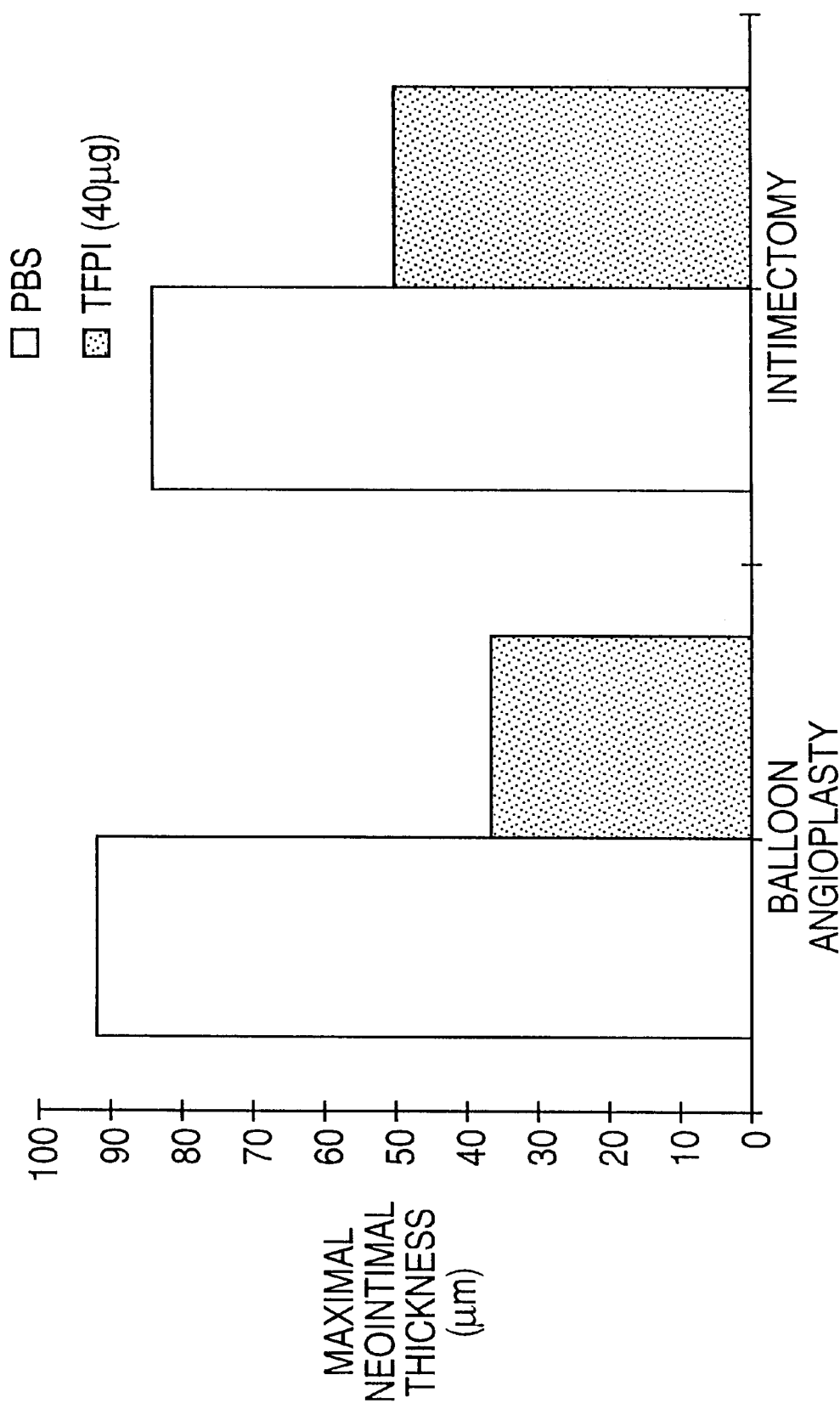
FIG. 1 is a bar graph which shows the maximal neointimal thickness in $\mu$m four weeks after arterial intervention for balloon angioplasty and intimectomy with TFPI treatment (40 $\mu$g/ml in PBS) vs untreated control (PBS).

In order to illustrate the invention in greater detail, the following illustrative Examples were carried out on laboratory rabbits:

The TFPI used in these Examples was obtained through recombinant DNA clones expressed in *E. coli*. It is a 277-amino acid protein consisting of the 276-residus sequence described by Wun et al., *J. Biol Chem.* 263, 6001–6004 (1988), and in U.S. Pat. No. 4,966,852, with a trivial modification whereby an additional alanine residue was inserted at the N-terminus as described in U.S. Pat. No. 5,212,091.

In sixteen (16) adult NZW rabbits in these Examples, the left common carotid artery was subjected to a balloon angioplasty; the right common carotid to an intimectomy and vascular anastomosis. Before restoring blood flow the vessels were irrigated with either 1 ml of control buffer or TFPI (40 µg/ml). With an elastin stain, maximal neointimal thickness was measured at both two and four weeks (n=4 for each group at each time point for each procedure). In eight additional rabbits, platelet deposition and the local persistence of gold-labeled TFPI (TFPI*) following a vascular anastomosis were followed by electron microscopy (EM) at 10' (min.) 24 hours, 72 hrs, and one week (n=2 at each time point).

There was no significant intimal hyperplasia at two weeks in either group following any of the procedures. At four weeks, the maximal neointimal thickness in control vessels injured by balloon angioplasty was 92.20±28.60 µm. Treatment with TFPI reduced the maximal lesion thickness 36.85±16.46 µm. In the intimectomized vessels at four weeks, the maximal neointimal thickness in control buffer-treated vessels was 84.83±23.94 µm. Local application with TFPI decreased the maximal neointimal thickness to 51.23±18.52 µm. Compared to control, all EMs during the first week showed lack of platelet aggregation and thrombus formation at the intimal surface and a persistence with a gradual decrease in the amount of TFPI* specifically bound to immature fibrin strands.

EXAMPLES

Materials and Methods

The National Institutes of Health "*Guide for the Care and Use of Laboratory Animals*" (Publication No. 86-23, revised 1985) was followed throughout these Examples. Adult New Zealand white rabbits (3.5–4 kg) were used in all experiments. Anesthesia was induced with an intramuscular injection of ketamine (15 mg/kg) and xylazine (5 mg/kg). All surgical procedures were carried out under sterile conditions.

Balloon Angioplasty. In sixteen (16) rabbits, a 2 cm segment of the right common carotid artery was exposed and isolated with a proximal and distal vascular clamp. A 2Fr. embolectomy catheter was inserted via an arteriotomy. The balloon was inflated and withdrawn three times, rotating the catheter 120 degrees after each pass to ensure uniform injury (48). The catheter was then removed and the arteriotomy site repaired. Prior to removing the clamps and restoring blood flow, the lumen was irrigated with 1 cc of either (a) control buffer (5 mM phosphate buffer) in eight (8) rabbits, or (b) TFPI (40 µg/ml) in the other eight (8) rabbits in a randomized and blinded fashion.

Intimactomy/Vascular Anastomosis. In the same sixteen (16) rabbits, the left common carotid artery was exposed and subjected to an intimectomy and a vascular anastomosis. The 3 cm segment of the artery was isolated with a proximal and distal vascular clamp. The artery was transected and the distal end everted. Using a microsurgical blade, 1 cm of intima was scraped off over 25% of the vessels circumference. The vessel was reverted and anastomosed using standard technique. Before placing the last stitch and restoring blood flow, 1 cc of control buffer-TFPI (40 µg/ml) was irrigated within the lumen.

Evaluation of Intimal Hyperplasia. Animals were sacrificed at both two and four weeks, and the vessels were harvested following perfusion fixation at physiologic pressure with 10% buffered formalin (n=4 for each group at both time points for each type of injury). The vessels were embedded, and serial transverse sections were stained with a modified Verhoeff van Gieson stain to visualize the elastin and delineate the junction between the intima and media. The point of maximal neointimal thickness was then measured using computerized image analysis.

TFPI-Binding and Electron Microscopy. In eight additional rabbits, the central ear artery was transected and anastomosed. Prior to restoring blood flow, the lumen gas irrigated with 1 ml of unconjugated gold particles or gold-labeled TFPI (TFPI*). The gold label was for enhancement of the electron microscopy. The vessels were harvested at 10 minutes, 24 hrs, 72 hrs, and one week, and fixed for electron microscopy (4% glutaraldehyde in 20 mM HEIPES-buffered Hank's saline, pH 7.35–7.4). The amount of platelet deposition and the local persistence of TFPI* were evaluated by EM (n=2 at each time point).

RESULTS

Balloon Angioplasty. There was no significant intimal hyperplasia at two weeks in either group. At four weeks, the maximal neointimal thickness in vessels injured by balloon angioplasty and treated with phosphate buffer was 92.20±28.06 µm. Treatment with TFPI reduced the maximal lesion thickness 36.83±16.46 µm.

Intimectomy. At two weeks, there was no significant intimal hyperplasia in either group At four weeks, the maximal neointimal thickness in phosphate buffer-treated vessels was 84.83±23.94µm. Local application with TFPI decreased the maximal neointimal thickness to 51.23±18.52 µm.

TFPI-Binding and Electron Microscopy. EMs of vessels treated with unconjugated gold particles showed numerous platelets adherent to the exposed elastic lamina and stands of fibrin clot within ten (10) minutes after injury. All EMs of vessels treated with gold-labeled TFPI during the first week showed lack of platelet aggregation and thrombus formation at the intimal surface, and a persistence with a gradual decrease in the amount of TFPI* specifically bound to immature fibrin strands.

Topical administration of the TFPI can be carried out by conventional methods of administration of topically effective drugs which are well known to persons skilled in the art. The TFPI is preferably administered from admixture with a physiologically acceptable vehicle or carrier, e.g, normal saline or buffered saline, such as phosphate-buffered saline or other such pharmaceutically acceptable buffers, e.g., HEPES and the like. The TFPI can also be administered in powder, salve or ointment form in conventional pharmaceutically acceptable vehicles. Such conventional vehicles and carriers are well known to the person skilled in the art, as can be seen by reference to numerous texts and treatises in the field of drug administration, e.g., *Remington's Pharmaceutical Sciences*, ed. Arthur Osol, 16th ed., 1980, Mack Publishing Co., Easton, Pa., or 18th ed., 1990. The amount of TFPI administered acutely and topically at the site and time of vascular injury can be a very small amount, depending in part on the degree and extent of the injury.

Doses of TFPI of from about 1 µg/ml to about 100 µg/ml in a volume of about 0.01 ml to about 1 ml applied at the injured site are suitable. It should be understood, however, that in some instances it may be desirable to administer a second dose, or to apply a sustained delivery of the TFPI for better inhibition of the intimal hyperplasia, although the inventors are not bound by this suggestion.

Figure 2:
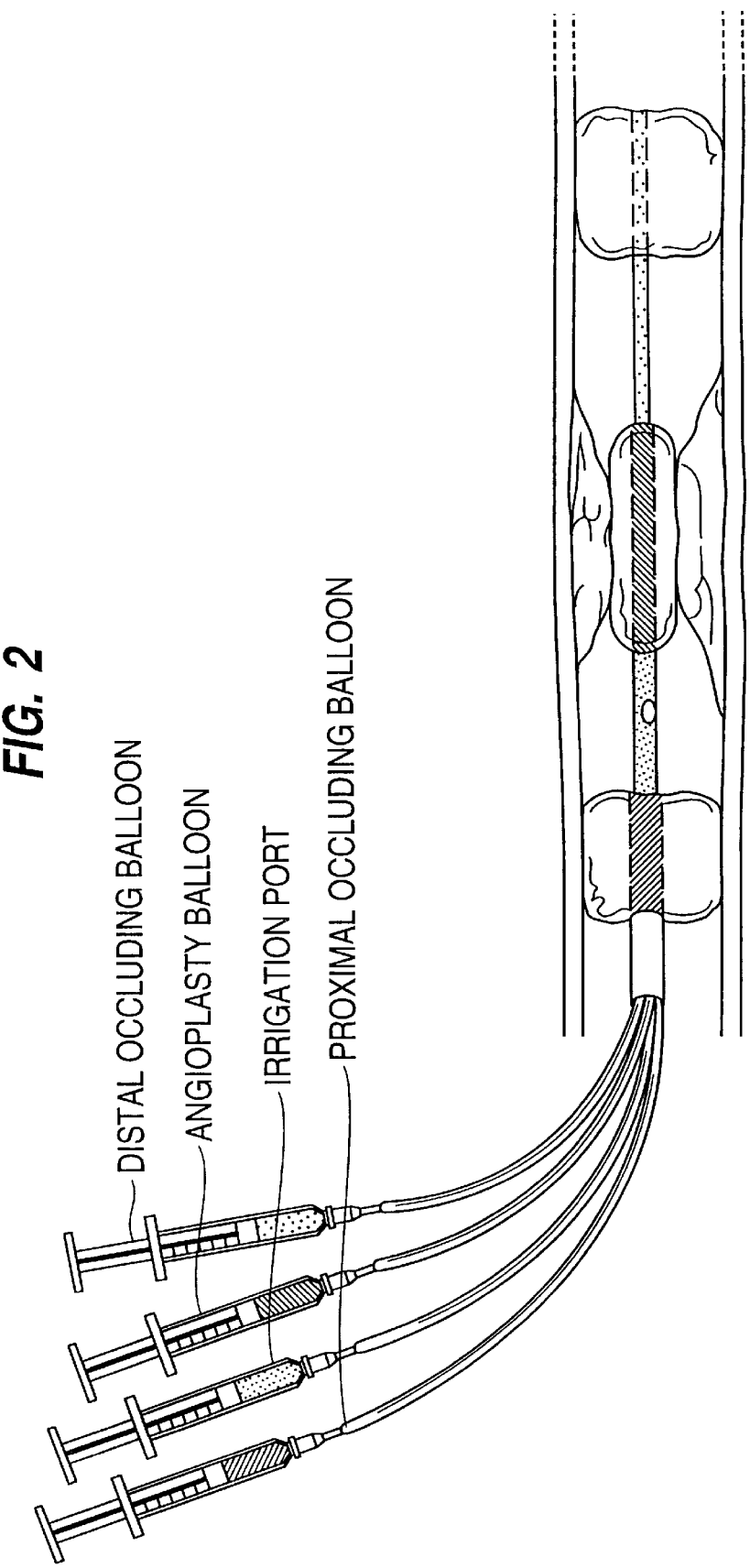
FIG. 2 is a sketch of one embodiment of the method of the invention for delivery of TFPI to the site of the vascular injury in which the arterial intervention is a balloon angioplasty.
Figure 3:
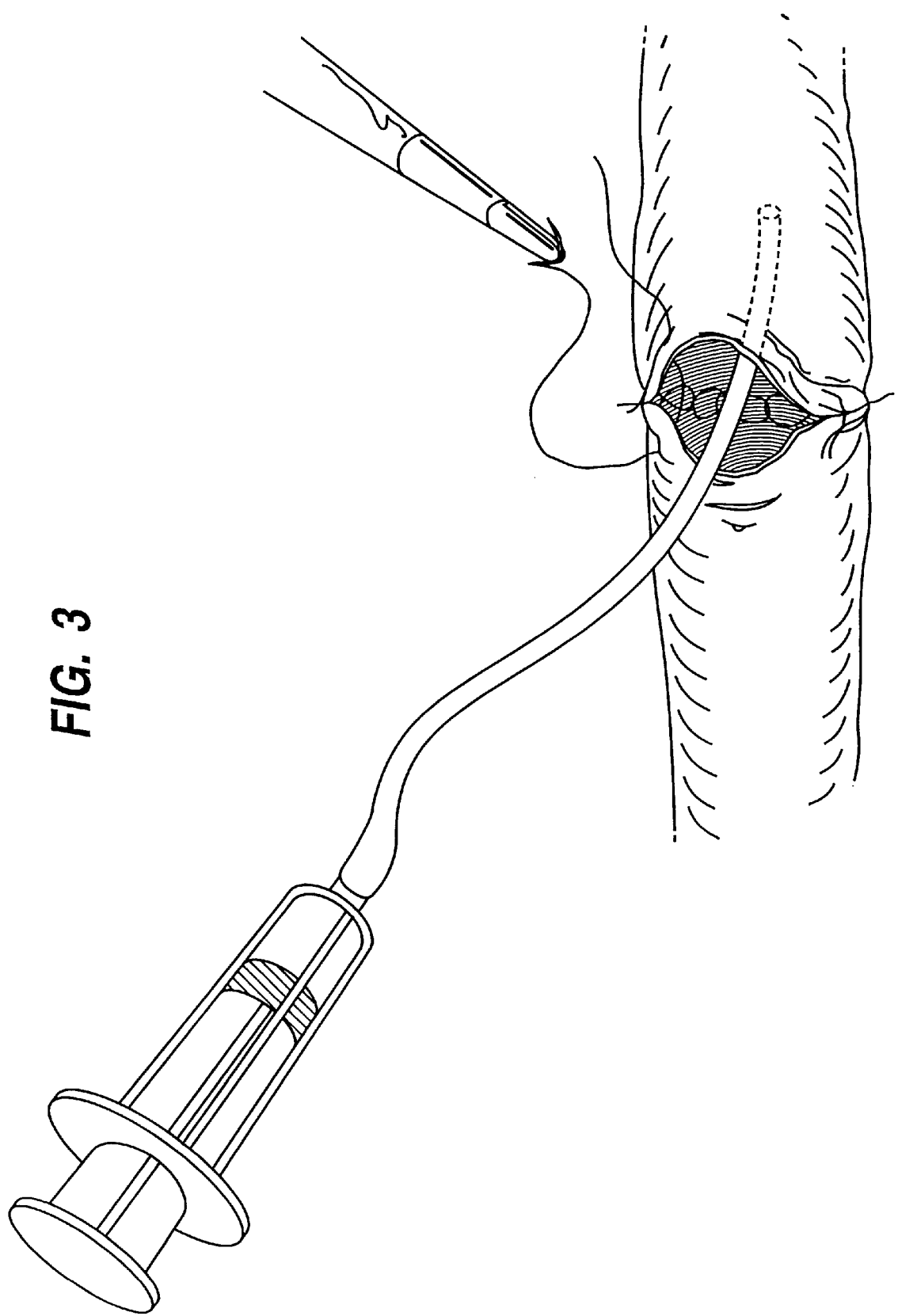
FIG. 3 is a sketch of another embodiment of the method of the invention for delivery of TFPI to the site of the vascular injury in which the arterial intervention is a vascular anastomosis.

The administration of TFPI according to the method of the invention is further illustrated by the two procedures shown in FIGS. 2 and 3. When the arterial intervention procedure is performed percutaneously, then a catheter device similar to that shown in FIG. 2 is preferably used for delivery of the TFPI; whereas, when the arterial intervention procedure is performed openly with exposure of the vessel, then a catheter device similar to that shown in FIG. 3 is preferably used for delivery of the TFPI.

In FIG. 2, a portion of the clogged artery is shown in which the procedure involves use of a four-fold catheter device. A distal occluding balloon and a proximal occluding balloon are used to isolate this portion of the artery and the clogged artery is subjected to the angioplasty balloon. A fourth catheter is shown for delivery of the TFPI through a larger port and/or smaller ports positioned along the length of the catheter.

In FIG. 3, a portion of the clogged artery is shown in which the procedure consists of a vascular anastomosis such as, e.g., bypass graft or endarterectomy. A catheter is shown for irrigating the lumen of the vessel at the site of the vascular injury by delivery of the TFPI prior to restoration of blood flow.

Various other examples will be apparent to the person skilled in the art after reading the present disclosure without departing from the spirit and scope of the invention. It will be understood that all such other examples are included within the scope of the appended claims.

REFERENCES

1. Califf, R M, Fortan, D F, Frid, D J, et al. Restenosis after coronay angioplasty: an overview. *J Am Coll Cardiol* 17:2B–13B, 1991.

2. Lytle, B W, Cosgrove, D, Loop, F D. *Cardiovasc Clin* 21(2):265, 1991.

3. North Anerican Symptomatic Carotid Endarterctomy Trial Collaborators. Beneficial effect of carotid endarterectomy in symptomatic patients with high-grade carotid stenosis. *N Engl J Med* 325:445453, 1991.

4. Gruentzig, A R, King, S B III, Schlumpf, M, and Siegenthaler, W. Long-term follow-up after percutaneous transluminal coronary angioplasty: the early Zurich experience. *N Engl J Med* 316:1127–1132, 1987.

5. Leimgruber, P P, Roubin G S, Hollman, J, et al. Restenosis after successful coronary angioplasty in patients with single-vessel disease. *Circulation* 73:710–717, 1986.

6. Hirshfeld, J W, Schwartz, I S, Jugo, R, et al. Restenosis after coronary angioplasty: a multivariate statistical model to relate lesion and procedure variables to restenosis. *J Am Coll Cardiol* 18:647–656, 1991.

7. Meier, B. Total coronary occlusion: a different animal? *J Am Coll Cardiol* 17 (suppl B):50B–57B, 1991.

8. Bell, M R, Berger, P B, Bresnahan, J F, Reeder, G S, Bailey, K R, Holmes, D R Jr. Initial and long-term outcome of 354 patients after coronary balloon angioplasty and total coronary artery occlusions. *Circulation* 85:1003–1011, 1992.

9. Cook, J M, Thompson, B W, Barnes, R W. Is routine duplex examination after carotid endarterectomy justified. *J Vasc Surg* 12:334–340, 1990.

10. European Coronary Surgery Study Group: Long-term results of prospective randomized study of coronary artery bypass surgery in stable angina pectoris. *Lancet* 2:1 73, 1982.

11. Bourassa, M G, Fisher, L D, Campeau, L, et al. Long-term fate of bypass grafts: The Coronary Artery Surgery Study (CASS) and Montreal Heart Institute experiences. *Circulation* 72:V-71–78, 1985.

12. Bourassa, M G, Campeau, L, Lesperence, S. Changes in grafts and coronary arteries after coronary bypass surgery. *Cardiovasc Clin* 21: 83, 1991.

13. Fitzgibbon, G M, Leach, A J, Kafker, H P et al. Coronary bypass graft fate: Longterm angiographic study. *J Am Coll Cardiol* 17:1075, 1991.

14. Lawrie, G M, Morris, G C Jr., Earle, N. Long-term results of coronary artery bypass surgery. Analysis of 1698 patients followed 15 to 20 years. *Ann Surg* 213:377, 1991.

15. Whittemore, A D, Clowes, A W, Couch, N P, et al. Second feromopopliteal reconstruction. *Ann Surg* 193:35, 1981.

16. Wengerter , K R, Veith F J, Gupia, S K, et al. Prospective ransomized multicenter comparison of in situ and reversed vein infrapopliteal bypasses. *J Vas Surg* 13:189–199, 1991.

17. Veith, F J, Gupta, S K, Ascer, E, et al. Six-year prospective multicenter randomized comparison of autologous saphenous vein and expanded polytetrafluoroethylene grafts in infrainguinal arterial arterial reconstruction. *J Vasc Surg* 3:104–114, 1986.

18. Clowes, A W, Reidy, M A, Clowes, M M. Mechanisms of stenosis after arterial injury. *Lab Invest* 49:208–215, 1983.

19. String, R J, String, R T. Recurrent carotid stenosis. *Surgery* 80:705–7110, 976.

20. Mcbride, W, Lange, R A, Hillis, L D. Restenosis after successful coronary angioplasty, pathophysiology and prevention. *N Engl J Med* 3 18:1734–1737, 1988.

21. Scharf, R, Harker, L. Thrombosis and atherosclerosis: regulatory role of interactions among blood components and endothelium. *Blut* 55:1131–1144, 1987.

22. Chesebro, J, Lam, J, Badimon, L, Fuster, V. Restenosis after arterial angioplasty: a hemorrheologic response to injury. *Am J Cardiol* 60 (suppl B): 10B–16B, 1987.

23. Chervu, A, Moore, W S. An overview of internal hyperplasia. *Surg Gynecol Obstet* 171:433–447, 1990.

24. Packham, M A, and Mustard, D F. The role of platelets in the development and complications of atherosclerosis. *Semin Hemaol* 23:8–26, 1986.

25. Ross, R. Atherosclerosis: a problem of the biology of arterial wall cells and their interactions with blood components. *Atherosclerosis* 1:293–3111, 1981.

26. Ross, R, Faggioto, A, Bowen-Pope, D, and Raines, E. The role of endothelial injury and the platelet and macrophage interactions in atherosclerosis. *Circulation* 70(suppl III):III-77–82, 1984.

27. Lange, P A, Willard, J E, Hillis, L D. Restenosis: the Achilles heel of coronary angioplasty. *Am J Med Sci* 306:265–275, 1993.

28. Mcbride, W, Lange, R A, Hillis, L D. Restenosis after successful coronary angioplasty, pathophysiology and prevention. *N Engl J Med* 318:1734–1737, 1988.

29. Liu, M W, Roubin, G S, King, S B. Restenosis after coronary angioplasty: potential biological determinants and role of intimal hyperplasia. *Circulation* 79:1374–1387, 1989.

30. Ip, J H, Fuster, V, Israel, D, et al. The role of platelets, thrombin and hyperplasia in restenosis after coronary angioplasty. *J Am Coll Cardiol* 17:77B–88B, 1991.

31. Ip, J H, Fuster, V, Badimon, L, et al. Syndromes of accelerated atherosclerosis: role of vascular injury and smooth muscle cell proliferation. *J Am Coll Cardiol* 15:1667–1687, 1990.

32. Wilcox, J N. Thrombin and other potential mechanisms underlying restenosis. *Circulalon* 84:432–435, 1991.

33. Linder, V, Lappi, D A, Baird, A, et al. Role of basic fibroblast growth factor in vascular lesion formation. *Circ Res* 68: 106–113, 1991.

34. Gasic, G P, Arenas, C P, Gasic, T B, Gasic G J. Coagulation factors X, Xa and protein S as potent mitogens of cultured aortic smooth muscle cells. *Proc Natl Acad Sci USA* 89:2317–2320, 1992.

35. Chen, L B, Buchanan, J M. Mitogenic activity of blood components, I: thrombin and prothrombin. *Proc Natl Acad Sci USA* 72:131–135, 1975.

36. Bar-Shavit, R, Benezra, M, Eldor, A, et al. Thrombin immobilized to extracellular matrix is a potent mitogen for vascular smooth muscle cells: nonenzymatic mode of action. *Cell Regul* 1:453–463, 1990.

37. Graham, D J, Alexander, J J. The effects of thrombin on bovine aortic endothelial and smooth muscle cells. *J Vasc Surg* 11:307–313, 1990.

38. Ross, R, Glomset, J, Kariya, B, et al. A platelet-dependent serum factor that stimulates the proliferation of arterial smooth muscle cells in vitro. *Proc Natl Acad Sci USA* 71:1207–1210, 1974.

39. Broze, G J Jr, Warren, L A, Novotny, W, et al. The lipoprotein-associated coagulation inhibitor that inhibits the factor VII-tissue factor complex also inhibits factor Xa: insight into possible mechanism of action. *Blood* 71:335–343, 1988.

40. Rao, L V M, Rapaport, S I. Studies on the mechanism of inactivation of the extrinsic pathway of coagulation. *Blood* 69:645–651, 1987.

41. Rapaport, S I. Inhibition of Factor VIIa/tissue factor-induced blood coagulation with particular emphasis upon a Factor Xa-dependent inhibitory mechanism. *Blood* 73:359–365, 1989.

42. Broze, G J Jr, Girard, T J, Novotny, W F. Regulation of coagulation by a multivalent Kunitz-type inhibitor. *Biochemistry* 29:7539–7546, 1990.

43. Rapaport, S I. The initiation of the tissue factor dependent pathway of blood coagulation. *Adv Exp Med Biol* 281:97–103, 1990.

44. Khouri, R K, Koudsi, B, Kaiding, F, et al. Prevention of thrombosis by topical application of tissue factor pathway inhibitor in a rabbit model of vascular trauma. *Ann Past Surg* 30:398–404, 1993.

45. Ornberg, R L, Deune, E G, Ozbeck, M R, Wun, T-C, and Khouri, R K. Localization of TFPI binding sites in an intimectomized microvessel. *Thromb Haemostas* (submitted).

46. Friedman, R J Stemermann, M B, Wenz, B, et al. The effect of thomboytopenia on exponential arteriosclerotic lesion formation in rabbits. *J Clin Inves.* 60:1191–1202, 1977.

47. Ragosta, M, Gimple L W, Gertz, SD et al. Specific factor Xa inhibition reduces restenosis after balloon angioplasty of atherosclerosis femoral arteries in rabbits. *Circulation* 89: 11262–127, 1994.

48. Stevens, S L, Hilgarth, K, Ryan, U S, Trachtenberg, J D, Choi, E T, and Callow, A D. The synergistic effect of hypercholesterolemia and mechanical injury on intimal hyperplasia. *Ann Vasc Surg* 6:55–61, 1992.

49. Ferns, G A A, Raines, E W, Sprugel, K H, et al. Inhibition of neointimal smooth muscle accumulation after angioplasty by an antibody to PDGF. *Science* 253: 1129–1132, 1991.

50. Linderg V, Reidy, M A. Proliferation of smooth muscle cells after vascular injury is inhibited by an antibody against basic fibroblast growth factor. *Proc Nat Acad Sci USA* 88:3739–3743, 1991.

51. Castellot, J J Jr, Addonizio, M, Rosenberg, R, et al. Cultured endothelial cells produce a heparin-like inhibitor of smooth muscle cell growth. *J Cell Biol* 90:372–379, 1981.

52. Fritze, L M S, Reilly, C F, Rosenberg, R. An antiproliferative heparin sulfate species produced by postconfluent smooth muscle cells. *J Cel Bio* 1:1041–1049, 1985.

53. Berk, B C, Gordon, B, Alexander, R W. Pharmacologic roles of heparin and glucocorticoids to prevent restenosis after coronary angioplasty. *J Am Coll Cardiol* 17:111B–117B, 1991.

54. Pow, T K, Currier, S, Minihan, A C, et al. Low molecular weight heparin reduces restenosis after experimental angioplasty (abstr). *Circulation* 80 (suppl II): 65, 1989.

55. Okada, T, Bark, D H, Mayberg, M R. Localized release of perivascular heparin inhibits intimal proliferation after endothelial injury without systemic anticoagulation.

Neuroscience 26:892–897, 1989.

56. Schwartz, L, Bourassa, M G, Lesperance, J, eg al. Aspirin and dipyridamole in the prevention of restenosis after percutaneous transluminal coronary angioplasty. *N Engl J Med* 318:1714–1719, 1988.

57. White, C W, Knudson, M, Schmidt D, et al. Neither ticopidine nor aspirindipyridamole prevents restenosis post PTCA: results from a randomized placebo controlled multicenter trial (abstr). *Circulation* 76 (suppl IV):213, 1987.

58. Mufson, L, Black, A, Roubin, G, et al. A randomized trial of aspirin in PTCA: effect of high vs low dose aspirin on major complications and restenosis (abstr). *J Am Coll Cardiol* 11(suppl A):236A, 1988.

59. Schanzenbacher, P, Grimmer M, Maisch, B, et al. Effect of high dose and low dose aspirin on restenosis after primary successful angioplasty (abstr). *Circulation* 78 (suppl II):99, 1989.

60. Knudtson, M J, Flintoft, V F, Roth, D L, et al. Effect of short-term prostacyclin administration on restenosis after percutaneous transluminal coronary angioplasty. *J Am Coll Cardiol* 15:691–697, 1991.

61. Meier, B. Prevention of restenosis after coronary angioplasty: a pharmacological approach. *Eur Heart J* 10 (suppl G):64–68, 1989.

62. Ellis, S G, Roubin, G S, Wilentz, J, et al. Effect of 18 to 24-hour heparin administration for prevention of restenosis after uncomplicated coronary angioplasty. *Am Heart J* 117:777–792, 1989.

What is claimed is:

1. A method for inhibiting intimal hyperplasia, comprising:

administering to a mammal with a vascular injury site induced by angioplasty or endarterectomy an inhibitorily effective amount of tissue factor pathway inhibitor (TFPI) to said vascular injury site.

2. The method as recited in claim 1 wherein said TFPI is (ala-$^1$) TFPI (1–277) or native TFPI (1–276).

3. The method as recited in claim 1 wherein TFPI is the first or second Kunitz domain of said TFPI.

4. The method as recited in claim 1 wherein TFPI is the first and second Kunitz domain.

5. The method as recited in claim 1 wherein said vascular injury is induced by angioplasty.

6. The method as recited in claim 1 wherein said vascular injury is induced by endarterectomy.

7. The method as recited in claim 1 wherein said TFPI is administered to said vascular injury site before said vascular injury site is exposed to blood.

* * * * *